United States Patent [19]

Meserol et al.

[11] Patent Number: 4,962,021

[45] Date of Patent: Oct. 9, 1990

[54] ANALYTE DETERMINATION USING GEL INCLUDING A REAGENT SYSTEM REACTS WITH ANALYTE TO CHANGE TRANSMISSIVE PROPERTY OF GEL DETECTABLE BY LIGHT BEAM TRANSMITTED THROUGH GEL BY TOTAL INTERNAL REFLECTANCE

[75] Inventors: Peter M. Meserol, Montville; Philip Bernstein, Glen Ridge; Rita C. Prodell, Morris Plains; Gargi Gupta, Morris Plains, all of N.J.

[73] Assignee: Personal Diagnostics, Inc., Whippany, N.J.

[21] Appl. No.: 876,473

[22] Filed: Jun. 20, 1986

[51] Int. Cl.$^5$ .................... C12Q 1/00; C12M 1/00; G01N 33/00
[52] U.S. Cl. ...................... 435/7; 435/288; 435/291; 435/299; 435/808; 435/810; 436/527; 436/530; 436/531; 436/165; 436/805; 436/808; 422/57; 422/58; 422/61
[58] Field of Search ............ 435/4, 7, 808, 291, 435/288, 289, 173, 299, 300, 301, 810; 436/164, 169, 518, 805, 165; 422/68, 55, 61, 102, 57, 58

[56] References Cited

U.S. PATENT DOCUMENTS

| | | | |
|---|---|---|---|
| 3,992,158 | 11/1976 | Przybylowicz | 435/808 X |
| 4,041,932 | 8/1977 | Fostick | 436/163 X |
| 4,144,306 | 3/1979 | Figueras | 436/170 X |
| 4,169,676 | 10/1979 | Kaiser | 422/68 X |
| 4,250,257 | 2/1981 | Lee et al. | 435/299 X |
| 4,399,099 | 8/1983 | Buckles | 422/68 X |
| 4,411,989 | 10/1983 | Grow | 435/291 X |
| 4,461,829 | 7/1984 | Greenquist | 436/530 |
| 4,540,660 | 9/1985 | Harte et al. | 436/518 |
| 4,587,102 | 5/1986 | Nagatomo et al. | 435/805 X |

Primary Examiner—Christine Nucker
Assistant Examiner—William H. Beisner
Attorney, Agent, or Firm—R. Gale Rhodes, Jr.

[57] ABSTRACT

A gel body is provided with a reagent system which interacts with a sample portion which diffuses into the gel to change the tranmissive properties of the gel. The gel body is used in an assay for various analytes, and preferably has a shape and index of refraction whereby a beam of light can be transmitted through the gel body by total internal reflectance.

29 Claims, 3 Drawing Sheets

ANALYTE DETERMINATION USING GEL INCLUDING A REAGENT SYSTEM REACTS WITH ANALYTE TO CHANGE TRANSMISSIVE PROPERTY OF GEL DETECTABLE BY LIGHT BEAM TRANSMITTED THROUGH GEL BY TOTAL INTERNAL REFLECTANCE

BACKGROUND OF THE INVENTION

This invention relates to the determination of analytes, and more particularly to an apparatus, product and process for detecting or determining analytes.

There are a wide variety of tests for determining various analytes, some of which depend on a color or turbidity change for detecting the presence or quantity of an analyte.

In a system which depends on a color change for detecting the presence or quality of analyte, the analyte interacts with a reagent system to produce a color change, and the rate of color change or intensity of color after a fixed time is measured as a measure of analyte.

Such a system has been employed for determining a wide variety of materials, such as glucose, various enzymes, etc.

Although such systems are generally effective for detecting analyte, there is a need for improving such systems, and in particular, for simplifying such systems so as to eliminate the necessity for handling a wide variety of reagents, while maintaining high accuracy.

SUMMARY OF THE INVENTION

In accordance with one aspect of the present invention, there is provided a product which is useful for determining an analyte, wherein an optically transparent gel body is provided with a reagent system, which in the presence of a sample portion which diffuses into the gel body changes the transmissive properties of the gel body, and wherein the gel body is supported by a support in a manner such that sample is applied to a first surface portion of the gel body, and a light source is directed for entry into the gel body through a second surface portion of the gel body for transmission through the gel for subsequent measurement and determination of analyte.

In accordance with the further aspect of the present invention the gel body is provided with an index of refraction such that the relative index of refraction of the gel body at its interface with the surrounding medium (e.g. air) is less than unity whereby upon a beam of light passing through the gel body and contacting the interface at an incident angle above the critical angle, the beam of light is reflected back into the gel body. In accordance with a still further aspect of the present invention, the gel body may be provided with a shape, such as a prismatic shape in the form of a dove prism, to permit the beam of light to enter and exit the gel body perpendicularly with respect thereto to substantially eliminate refractance during entry and exit in addition to contacting the interface above the critical angle.

In accordance with a further aspect of the present invention, there is provided a process for determining an analyte which employs a gel body which includes a reagent system which changes at least one of the transmissive properties of the gel.

In accordance with a still further aspect of the present invention, there is provided a process for determining an analyte by an immunoassay wherein an unbound labeled ligand portion (tracer portion) produced in the assay is diffused into a gel body which contains a reagent system which in the presence of the tracer, changes the transmissive properties of the gel.

As yet a further aspect of the present invention, there is provided a reagent kit or package for determining an analyte by an immunoassay procedure wherein the kit includes a tracer and a gel body, which gel body includes a reagent system, which in the presence of the tracer changes at least one of the transmissive properties of the gel body.

More particularly, there is provided a gel through which light can be transmitted, and there is incorporated into the gel a reagent system, which in the presence of a sample portion, which diffuses into the gel, changes at least one of the transmissive properties of the gel. The gel is supported in a manner such that a sample can be applied to first surface portion of the gel body, and light directed for entry into the gel body through a second surface portion of the gel body for transmission through the gel body, whereby an assay may be conducted without removing the sample which has been applied to the gel body.

In this manner, sample may be applied to the gel, and a portion of the sample, which diffuses into the gel, interacts with the reagent system in the gel, and light transmitted through the gel is measured for determining analyte.

The change in at least one of the transmissive properties of the gel by use of a reagent system may be accomplished in a variety of ways, including for example, a change in light absorption, for example, a visible color change (formation of color or deletion of color), a change in UV absorption, etc.; change in turbidity, etc. The selection of a suitable reagent system should be apparent to those skilled in the art from the teachings herein.

Thus, a "change in the transmissive property of the gel" refers to the amount of light scattered or absorbed when a beam of light is directed through the gel, and generally depends on a change in turbidity or a change in energy absorption of the gel. Such change in transmissive property is generally measured by passing light through the gel, and determining the ratio of the intensity of transmitted or scattered light to the intensity of the incident light. The change in the transmissive property, i.e., the change in the amount of light absorbed or scattered in the gel is measured as a measure of analyte. Thus, for example, if the sample portion which is diffused into the gel is the analyte or a portion thereof, then as the concentration of the analyte increases, the change in transmissive property of the gel increases or decreases whereby the amount of light absorbed or scattered in the gel is proportional to the concentration of the analyte in the sample applied to the gel.

In accordance with yet another aspect of the present invention, there is provided a combination of an optically transparent container and optically transparent gel body including a reagent system, which reagent system in the presence of a sample portion which diffuses into the gel body changes at least one of the transmissive properties of the gel body, wherein a beam of light is transmitted through the gel body such that the angle of incidence of the light beam at the gel body-container interface, or the container-air interface, is above the critical angle for total internal reflectance at the interface and transmitted through the body of gel body by total internal reflectance. The critical angle $\theta_c$ for total internal reflectance is given by the following:

$$\theta_c = \sin^{-1} n_{12}$$

where (Note FIG. 1) $n_{12}$ is the relative index of refraction at the interface I between the internal medium $M_1$ and the external medium $M_2$ and is less than unity; where $n_{12} = n_1/n_2$, and where $n_1$ is the index of refraction of the internal medium $M_1$ through which the beam of light L is transmitted obliquely, and where $n_2$ is the index of refraction of the external medium $M_2$ towards which the beam of light is being transmitted obliquely.

To further enhance transmission of the light beam through the gel body by total internal reflectance and to substantially eliminate light beam refraction upon entry and exit, the inner and outer surfaces of the container and the gel body are given a prismatic shape (e.g. dove prism shape) to permit the beam of light to enter and exit the container and gel body perpendicularly with respect thereto and also contact the interface of interest at an incident angle greater than the critical angle.

In accordance with a preferred embodiment of the invention, the reagent system which is included within the gel is a chromogen system which produces a change in light absorption (in the visible or UV region) in the presence of a sample portion which diffuses into the gel. In accordance with this aspect of the present invention, the sample portion which diffuses into the gel is the analyte, whereby measuring a change in transmissive property of the gel caused by interaction of the analyte and the chromogen reagent system may be used to measure the presence and or quantity of analyte in a sample applied to the gel. It is to be understood, however, that as hereinafter described in more detail, the sample portion which is diffused into the gel may be a tracer used in an immunoassay procedure, whereby the change in the transmissive properties of the gel caused by interaction between the tracer and the reagent system within the gel is used to measure the presence and-/or concentration of analyte in an original sample, rather than the presence and/or concentration of the tracer which directly contacts the reagent system within the gel.

The gel which is used is one which has a clarity such that there is a minimum scattering of light, and should also be stable so that there is minimal syneresis. In addition, the gel should have a porosity such that the material which is to change at least one of the transmissive properties of the gel in the presence of the reagent system diffuses into the gel within the time period in which the assay is to be conducted. Such gels are generally known in the art, and include polyacrylamide, plant and animal gels such as agarose, gelatin, etc. Gels are formed from polymers or long chain molecules cross-linked to create a tangled network in which a liquid medium is entrapped, the liquid prevents the network from collapsing into a compact mass and the network prevents the liquid from flowing away. The reagent system which is within the gel may be dissolved in the liquid medium, may be suspended therein or bound to the gel matrix. In many cases, the solvent portion of the gel is water. The selection of an appropriate gel is deemed to be within the scope of those skilled in the art from the teachings herein.

The support or container, which may be in the form of a cuvette or container for the gel, can be formed from a wide variety of optically transparent materials which transmit light, including, but not limited to, glass, quartz, various plastics, and the like. The selection of a suitable support or container for the gel body, which includes the reagent system, is deemed to be within the scope of those skilled in the art from the teachings herein.

In accordance with a preferred embodiment, the support holds the gel body in a manner such that a sample may be applied to a first surface of the gel, and light directed for entry into the gel body through a second surface of the gel, whereby the sample need not be removed from the gel prior to completion of the assay. The second surface is generally a surface of the gel which is not opposite the first surface of the gel whereby the first and second surfaces are angularly positioned with respect to each other, most preferably at an angle other than 90° (acute or obtuse). This is particularly advantageous in that it has been found that the gels are capable of selectively diffusing portions of an entire sample into the gel, whereby samples, such as whole blood, or saliva may be applied to the gel, without the necessity of removing particulates from such samples, and without the necessity for removing such sample from the gel prior to completion of the assay. Thus, for example, in an assay employing a body fluid such as blood, it is not necessary to separate plasma or serum from cells, prior to conducting the assay, and whole blood may be applied to the gel, and the assay conducted without removing the blood sample from the gel surface. Thus, in accordance with this aspect of the invention, the analyte present in whole blood is diffused into the gel, and the cells remain on the gel surface. The assay may be accomplished by transmitting light through a surface of the gel different from the surface of the gel to which sample was applied, thereby eliminating serum (or plasma)—cell separation and also eliminating sample removal from the gel. It is to be understood that it is possible for the first and second surface portions to be different portions of the same surface; however, in the preferred embodiment the first and second surface portions are on different surfaces.

The gel body may be employed for determining a wide variety of analytes which are capable of interacting with a reagent system which will produce a detectable change in the transmissive properties of the gel body. As examples of such analytes, there may be mentioned glucose, uric acid, cholesterol, creatinine, lactate dehydrogenase (LDH), triglycerides, immunoglobulins, (antigens and/or antibodies) acetyl-cholinesterases, alanine amino transferase (ALT), aspartate aminotransferase (AST) creatine phosphokinase (CPK), ethanol, total protein, albumin, calcium, bilirubin, blood urea nitrogen (BUN), alkaline phosphatase, peroxidase; N-acetyl-B-D-glucosaminidase (NAG), B-D-glucuronidase, etc.

The reagent system placed in the gel is a chemical system which contains one or more reagents which in the presence of a sample portion which diffuses into the gel produces a change in at least one of the transmissive properties of the gel. The reagent system will depend on the analyte to be determined, and whether the change in the transmissive properties to be measured is due to a change in color, UV absorption or turbidity of the gel. In a colormetric assay, where the change in transmissive properties is due to a change in light absorption, a chromogenic reagent system is employed. In a turbidmetric or nephelometric system, where the change in the transmissive properties results from light being blocked or scattered by a suspension of particles, a turbidmetric reagent system is incorporated into the gel.

The colorimetric reagent system which is incorporated into the gel body may be any one of a wide variety of chromogenic reagent systems which are conventionally utilized for colorimetrically determining analytes and such systems are generally described in the literature, and are also commercially available. As representative chromogenic reagent systems, including both end point and kinetic determinations, there may be mentioned oxidase reaction systems, NADH-NAD reaction systems, hydrolytic reaction systems etc. For example, in an oxidase reaction system, oxidative enzymes react with the sample portion which diffuses into the gel body to produce a change in the colorimetric properties of the gel body as an indication of presence and/or amount of analyte. An NADH/NAD reaction system relies upon the reduction of NAD to NADH or the oxidation of NADH to NAD, which can be determined in the UV range, or in the alternative, NADH is caused to react with a dye system to produce a visible change in the color properties of the gel body as a measure of analyte. As a further example of a colorimetric reagent system, there may be mentioned a chromogen which directly interacts with a sample portion to produce a color change, such as interaction between alkaline phosphatase and a chromophore containing a hydrolyzable phosphate group, with hydrolysis of the phosphate group by the phosphatase producing a change in color. As still a further example, there may be mentioned a peroxide and an oxidizable chromogen. As hereinabove indicated, a wide variety of colorimetric systems are known in the art, and such colorimetric reagent systems may be incorporated into the gel body in accordance with the present invention. Such reagent systems are incorporated into the gel body in an amount which is effective to produce a detectable change in the colorimetric properties of the gel in the presence of the sample portion which is diffused into the gel. Such effective amounts may be determined by those skilled in the art from the teachings herein.

In addition, the reagent system will include suitable buffers and the like to provide for interaction between the sample portion which diffuses into the gel, and the reagent system. The selection of suitable amounts and concentrations, as well as optimum pH for various colorimetric systems is deemed to be within the scope of those skilled in the art from the teachings herein.

As hereinbefore indicated, the gel indicator system is produced by forming a solution, (preferably in water) of the reagents which are to be used as the reagent system for changing the transmissive properties of the gel, combining such a solution with a gel stock, such a agarose in water, and placing the mixture on or in a suitable support, such as a container or cuvette, having the desired refractive index and shape. As hereinabove indicated, the support for the gel preferably supports the gel body, including the reagent system, in a manner such that a sample is applied to a first surface of the gel, and a light source is directed against a second surface of the gel.

In an assay, a sample is applied to a surface of the gel body, and all or a portion of the sample diffuses into the gel. As hereinabove indicated, at least the portion of the sample which interacts with the reagent system diffuses into the gel.

A beam of light is then directed against a surface portion of the gel body different than the surface portion to which sample is applied, and in accordance with a preferred embodiment, the light is transmitted through the gel by total internal reflectance. A detector is positioned with respect to the gel body in the optical light path of the light transmitted through the gel in order to detect the change in the transmissive properties of the gel.

In the case of a reagent system which produces a visible color change, a "yes-no" assay may be effected without directing light in a specific manner and without using an optical detector.

In the case of a light absorption assay wherein the analyte in the sample interacts with the reagent system to change light absorption, as the amount of analyte in the sample increases, the change in light absorption caused by interaction between analyte and the reagent system increases or decreases, which decreases or increases a transmissive property of the gel. Such a change in transmissive property of the gel is proportional to the amount of analyte in the sample, whereby by use of appropriate standard curves, the quantity of analyte in the sample can be determined.

The assay may be a kinetic assay (detecting rate of change of the transmissive properties of the gel) or may be an end point assay, (change of the transmissive properties of the gel after a fixed period of time). In accordance with a preferred embodiment, the assay is effected kinetically.

It is to be understood that the present invention may be employed to determine the presence of analyte in a sample, rather that quantity of analyte in a sample.

Although a preferred embodiment of the present invention involves changing at least one transmissive property of the gel body by change in color, it is to be understood that the transmissive property or properties of the gel body may be changed by turbidity by use of a reagent system which interacts with a portion of the sample to change turbidity. Thus, for example, in an assay for rheumatoid factor, gamma globulin may be employed as the reagent in the gel. A sample containing rheumatoid factor will interact with the gamma globulin and increase turbidity. This assay and others are within the scope of the invention.

Applicant has found that chromogens which produce color in the visible range may be effectively incorporated into a gel body, and when so incorporated, such chromogens have improved stability. Thus, for example, it is possible to incorporate chromogens which provide color in the visible range such as 2,2'-Azinobis(3-ethybenzthiazoline sulphonic Acid) often referred to as ABTS, or a tetrazolium salt, such as, 2, 2'$^0$ Di-p-nitrophenyl-5, 5'-diphenyl-3,3' [3,3'-dimethoxy-4,4'-diphenylene] ditetrazolium chloride into a gel so as to provide a color change in the visible range, without the stability problems heretofore encountered in using such chromogens in an aqueous state.

As hereinabove indicated, in accordance with another aspect of the invention, there is provided an immunoassay which utilizes a gel body containing a reagent system which interacts with tracer to change at least one of the transmissive properties of the gel body. Although the term "immunoassay" has been employed, the term immunoassay is employed in a generic sense, and encompasses competitive protein binding assays which strictly speaking are not immunoassays.

In accordance with this aspect of the present invention, as known in the art, in an immunoassay, there is produced a bound tracer portion, and an unbound (free)

tracer portion, and analyte is assayed by determining at least one of the free and bound tracer portions produced in the assay. In accordance with this aspect of the present invention, the free tracer portion formed in the assay is allowed to diffuse into the gel body, wherein the free tracer portion interacts with a reagent system incorporated into the gel which changes at least one of the transmissive properties of the gel.

The change in the transmissive property or properties of the gel is then compared with a standard curve so as to provide a quantitative determination of analyte. Alternatively, analyte may be qualitatively determined by the procedure of the invention; e.g. a "yes-no" assay.

As known in the art, the tracer which is used in the assay is a ligand coupled or conjugated to a detectable marker, and in accordance with this aspect of the present invention, the detectable marker of the tracer interacts with the reagent system in the gel body to produce a change in at least one of the transmissive properties of the gel body.

Thus, for example, in a so called competitive assay, analyte and tracer compete for binding sites on a binder for the analyte and tracer, such as an antibody or a naturally occuring binder, with the amount of tracer which becomes bound to the binder being inversely proportional to the amount of analyte in the sample. Similarly, the amount of tracer which remains unbound (free) is directly proportional to the amount of analyte in the sample.

In accordance with the present invention, the free tracer portion is allowed to diffuse into the gel body wherein the free tracer portion interacts with the reagent system to change at least one of the transmissive properties of the gel. The change in the transmissive properties of the gel body is directly proportional to the amount of analyte in the sample in that the amount of tracer in the free tracer portion is directly proportional to the amount of analyte in the sample.

The bound and free tracer portions may be separated from each other by procedures known in the art. Thus, for example, the assay may be a so called solid phase assay wherein the binder is bound to a solid support, whereby the tracer which is bound to the binder may be easily separated from the unbound tracer by separating the solid phase from the sample, and applying the sample to the gel so as to permit the free tracer to diffuse into the gel body.

In accordance with a preferred embodiment of the present invention, a competitive assay may be effected in solution to form both a bound and free phase, and the entire sample applied to the gel, with the properties of the gel being such that the free tracer diffuses into the gel body, with the bound tracer remaining on the gel surface; for example, by appropriate selection of gel porosity. In this manner, analyte in the sample may be determined, as hereinabove described, without prior separation of the bound and free phases formed in the assay.

In accordance with another type of assay, generally referred to as a "sandwich" assay, there is provided in the assay system a binder for the analyte, and a tracer, wherein the tracer is bound by the analyte i.e., the tracer is comprised of a binder for the analyte conjugated to a detectable marker. In such an assay system, the analyte is bound to the binder, and the tracer is bound to the analyte, bound to the binder. By using an excess of tracer, there is produced a tracer bound to analyte, which is bound to binder (bound tracer phase) and a free tracer phase (unbound tracer). The amount of tracer which is in the bound phase is directly proportional to the amount of analyte in the sample, and the amount of tracer which remains unbound is indirectly proportional to the amount of analyte in the sample. Similarly to a competitive type of assay, the free tracer portion is diffused into the gel body to interact with the reagent system to produce a change in at least one of the transmissive properties of the gel body. In such an embodiment, the change in transmissive property or properties of the gel body is indirectly proportional to the amount of analyte in the sample.

As in the competitive type of assay, the bound and free phases may be separated by techniques in the art, such as by supporting the binder on a solid support. Alternatively, in accordance with a preferred embodiment of the present invention, the bound and free phases may be separated on the gel in that by controlling the porosity of the gel, essentially only the free tracer diffuses into the gel body under the assay conditions, with the bound tracer phase essentially remaining on the surface of the gel.

Although the present invention has been described generally with respect to so called sandwich and competitive assays, it is to be understood that the procedure of the present invention is also applicable to other assay procedures. Thus, for example, the present invention may be used for a sequential assay in which a binder for both the analyte and tracer is sequentially contacted with the analyte and tracer; a reverse sandwich assay, a simultaneous sandwich assay, etc.

In all of such assays, the free tracer portion is caused to interact with the reagent system in the gel body to change at least one of the transmissive properties of the gel body, which change is measured to determine analyte (qualitative or quantitative) in the sample being assayed.

The detectable marker which is preferably employed in forming the tracer is an enzyme in that an enzyme may be colorimetrically determined in the gel body by reagent systems generally known in the art. In accordance with the present invention, the reagent system which is included within the body of the gel will be a reagent system which interacts with the enzyme used as the marker of the tracer to produce a change in the transmissive property or properties of the gel body by a change in light absorption. Thus, for example, a peroxidase enzyme marker may be detected by use of hydrogen peroxide and an appropriate chromogen which is oxidized by the oxygen generated by interaction between the peroxidase and hydrogen peroxide. Similarly, a phosphatase enzyme marker may be detected by use of a chromogen of the type hereinabove described which produces a color change by interaction with alkaline phosphatase. The colorimetric systems for producing a detectable change in light absorption by interaction with an enzyme are well known in the art and no further details in this respect are deemed necessary for a complete understanding of the present invention.

The immunoassay technique of the present invention may be employed for determining a wide variety of analytes. As representative examples of such analytes, there may be a mentioned various hormones such as LH, HCG, TSH, etc., analytes such as T4; T3; steroids, such as digoxin, digoxegenin; various bacteria and viruses; CEA; various antibodies associated with bacteria and viruses; drugs, including drugs of abuse and therapeutic drugs; for example, theophylline; etc. The analytes which can be determined by the procedure of the present invention should be apparent to those skilled in the art from the teachings herein.

In a representitive assay, in which the tracer is a ligand labeled with an enzyme, such as, for example, a peroxidase, the gel body contains a reagent system which includes hydrogen peroxide and a suitable chromogen which produces color upon being oxidized by oxygen released by interaction of the hydrogen peroxide and the peroxidase marker of the tracer. The hydrogen peroxide would be preferrably incorporated into the gel body in a stabilized form such as, for example, mannitol, urea, etc. stabilized hydrogen peroxide.

In a typical competitive assay procedure, the enzyme labeled ligand, which is either the analyte or appropriate analog of the analyte (an appropriate analog is a ligand which is bound by the binder for the analyte) is combined with sample containing or suspected of containing the analyte and a binder for both the analyte and the tracer such as, for example, an antibody. After a suitable contact time, there is produced in the assay solution a bound tracer phase, and a free tracer phase. The entire sample is then applied to a surface of the gel body, with the free tracer phase diffusing into the gel body and interacting with the reagent system to produce a change in the transmissive property or properties of the gel by development of color. The rate at which the color is formed, or the intensity of the color, is directly proportional to the amount of analyte in the sample in that the free tracer which diffuses into the gel body is directly proportional to the amount of analyte in the sample; i.e., as the concentration of analyte in the sample increases, the concentration of free tracer in the sample increases. Thus, in this assay procedure, the gel body functions to provide a stable environment for the reagent system, and avoids the necessity of mixing reagents for colorimetrically determining the enzyme labeled tracer. Moreover, the gel body can function to separate the bound and free phases formed in the assay.

As known in the art, by comparing the measured amount of light transmitted through the gel body, with a standard curve, the concentration of analyte in the sample can be determined.

Thus, in accordance with the present application and claims, a sample portion which diffuses into the gel may be the analyte or a material which is indicative of the presence and/or amount of analyte.

The invention will be described with reference to the following examples; however, the scope of the invention is not to be limited thereby. Unless otherwise specified, all parts are by weight.

DETAILED DESCRIPTION OF THE PREFERRED EMBODIMENTS

EXAMPLE I

Figure 1:
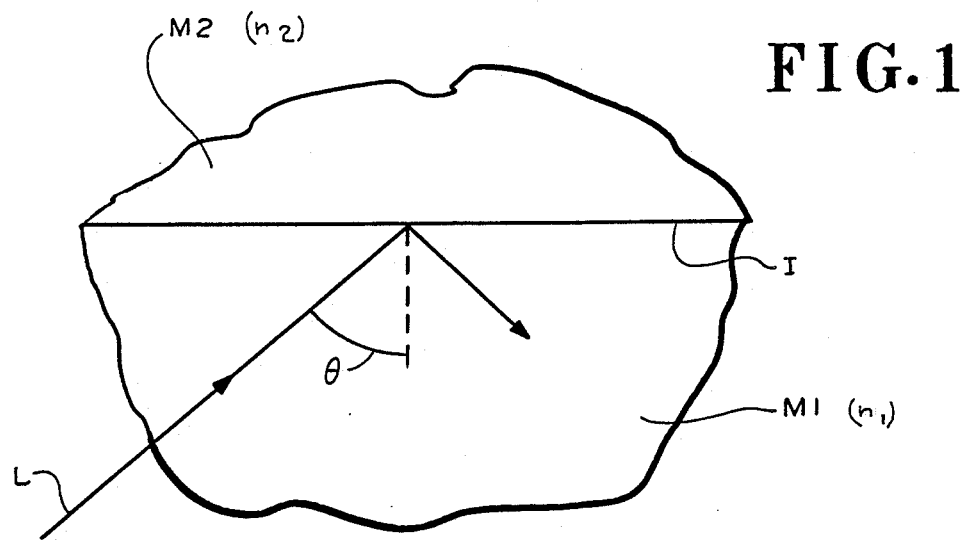
FIG. 1 illustrates the relative index of refraction of a beam of light at the interface between two mediums.

To prepare the necessary reagents analytical grade chemicals and water should be employed. All glassware should be cleaned by acid washing. The buffer used for this example is 0.1M acetate buffer which is made by carefully weighing 8.2 g. sodium acetate, anhydrous, and dissolving it in about 900 ml. reagent grade water in an analytical volumetric flask. The sodium acetate must be dissolved completely and the pH at 30° C. should be adjusted to 4.4 by the addition of acetic acid. After the correct pH has been achieved, the volume of buffer should be brought to exactly 1000 ml. with reagent grade water. The buffer must be stored in a closed container to minimize carbon dioxide absorption.

To prepare the ABTS stock solution weigh out 11.0 mg of ABTS and place it in a 10 ml. analytical volumetric flask. Carefully add 0.1M acetate buffer and adjust the volume to exactly 10 ml. This reagent should be oxygenated by bubbling oxygen through the solution for at least five minutes.

To prepare the hydrogen peroxide stock solution, weigh out 600 mg. hydrogen peroxide.mannitol and place it in a 10 ml. analytical volumetric flask. Dissolve the powder in about 8 ml. 0.1M acetate buffer and carefully adjust the volume to exactly 10 ml.

To prepare the gel stock weigh out 600 mg. agarose (ME) (or other gelling medium) and dissolve by heating in 50 ml. 0.1M acetate buffer.

To prepare the final gel combine 4 volumes of gel stock with 3 volumes of ABTS stock and 3 volumes of hydrogen peroxide.mannitol stock that have been mixed. Mix well and distribute the gel in a known quantity onto surfaces that have a different index of refraction and conformation and allow to harden. Variation in the amounts and ratios of stock reagents may be made if desired, e.g., one half the amount or concentration of ABTS and/or hydrogen peroxide.mannitol may be employed while still retaining excellent reactivity.

To test the analyte for the presence of peroxidase, a sample of the material is placed on a gel surface and diffusion of the analyte will occur into the porous reagent gel. As the enzymatic reaction progresses, a change in the transmissive characteristic or characteristics of the gel will occur resulting in a change in color that may be rapidly detected at 412 nm by instrumentation employing internal reflectance. This change will also be detectable by visual means.

EXAMPLE II

The buffer used for this example is 0.1M potassium phosphate pH 6.0±0.05. Carefully weigh 13.61 g potassium phosphate monobasic and dissolve it in a 1000 ml capacity analytical volumetric flask containing about 900 ml reagent grade water. To this add a few crystals of dibasic potassium phosphate to adjust the pH to 6.0. After adjustment dilute the volume with reagent grade water to exactly 1000.0 ml. To prepare peroxidase stock solution weigh 6.0 mg peroxidase having a unitage of about 150–200 units per mg solid, dissolve in approximately 8 ml reagent grade water contained in a 10 ml analytical volumetric flask and then bring the volume to exactly 10.0 ml with reagent grade water. To prepare glucose oxidose stock solution, weigh 0.2 mg glucose oxidase in approximately 8 ml reagent grade water contained in a 10 ml analytical volumetric flask and then bring the volume to exactly 10 ml with reagent grade water.

To prepare the ABTS stock solution weigh 20 mg ABTS, dissolve in approximately 8 ml of the 0.1M potassium phosphate buffer contained in a 10 ml analytical volumetric flask and then bring the volume to exactly 10 ml with 0.1M potassium phosphate buffer.

To prepare the gel stock, weigh out 600 mg agarose (ME) (or other gelling medium) and dissolve by heating in 50 ml 0.1M potassium phosphate buffer.

To prepare the final gel combine 4 volumes of gel stock with 2 volumes of glucose oxidase stock and 2 volumes of peroxidase stock and 1.5 volumes buffer and 0.5 volume ABTS stock. Mix well and distribute the gel in a known quantity onto the surfaces that have a different index of refraction and conformation and allow to harden.

Variations in the amounts and ratios of stock reagents may be made if desired, e.g., one half the amount or concentration of ABTS, glucose oxidase and/or peroxidase may be employed while still retaining excellent reactivity.

To test the analyte for the presence of glucose, a sample of the material, such as a drop of blood, is placed on a gel surface and diffusion of the non-particulates will occur into the porous reagent gel. As the enzymatic reaction progresses, a change in at least one of the transmissive characteristics of the gel will occur resulting in a change of color that may be rapidly detected at 412 nm by instrumentation employing internal reflectance. This change will also be detectable by visual means.

EXAMPLE III

To prepare the stock buffer, in this example, a phosphate buffer, pH 8.0±0.05, weight out 3.522 g potassium phosphate, monobasic and 5.742 g sodium phosphate, dibasic and place the salts in a 1000 ml capacity analytical volumetric flask with about 900 ml reagent grade water to dissolve. After solution is achieved, adjust the pH to 8.0 by adding 1N sodium hydroxide solution and bring the volume to exactly 1000 ml with additional reagent grade water.

To prepare the gel stock, weight out 600 mg agarose (ME) (or other gelling medium) and dissolve by heating in 50 ml phosphate buffer. To prepare the reactant antigen, dissolve a quantity of gamma globulin in phosphate buffer sufficient for detection of the antibody analyte. In the case of a liquid reactant, prepare a predetermined dilution of reactant, for example, 1 part of liquid gamma globulin to 3 parts phosphate buffer.

To prepare the final gel combine 4 volumes of gel stock with 6 volumes of reactant. Mix well and distribute the gel in a known quantity onto surfaces that have a different index of refraction and conformation and allow to harden.

To test the analyte for the presence of RF factor, a sample of analyte is placed on a gel surface and diffusion of the analyte will occur into the porous reagent gel. As the antibody-antigen reaction progresses a change in the transmissive characteristic or characteristics of the gel will occur that is detectable by instrumentation employing internal reflectance. When the serum from a person not having RF rheumatiod arthritis is tested, the transmissive characteristic or characteristics of the gel are relatively unchanged.

The present invention is advantagous in that there is provided a product and process in which various assays may be easily accomplished. In addition, the system provides improved stability for reagents. Furthermore, the assays may be conveniently and reliably accomplished.

These and other advantages should be apparent to those skilled in the art from the teachings herein.

Figure 2:
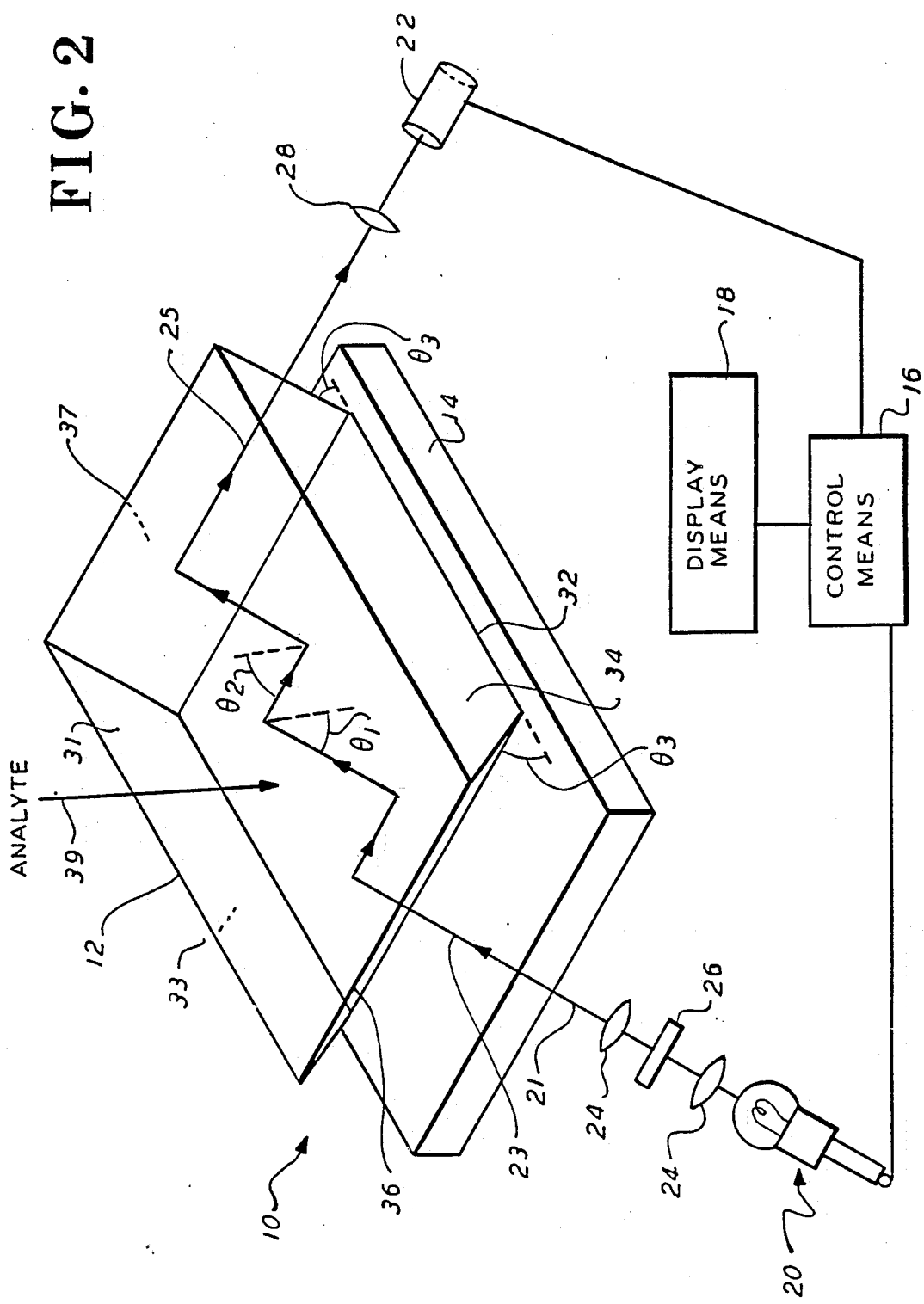
FIG. 2 illustrates a first embodiment of the instant invention.
Figure 3:
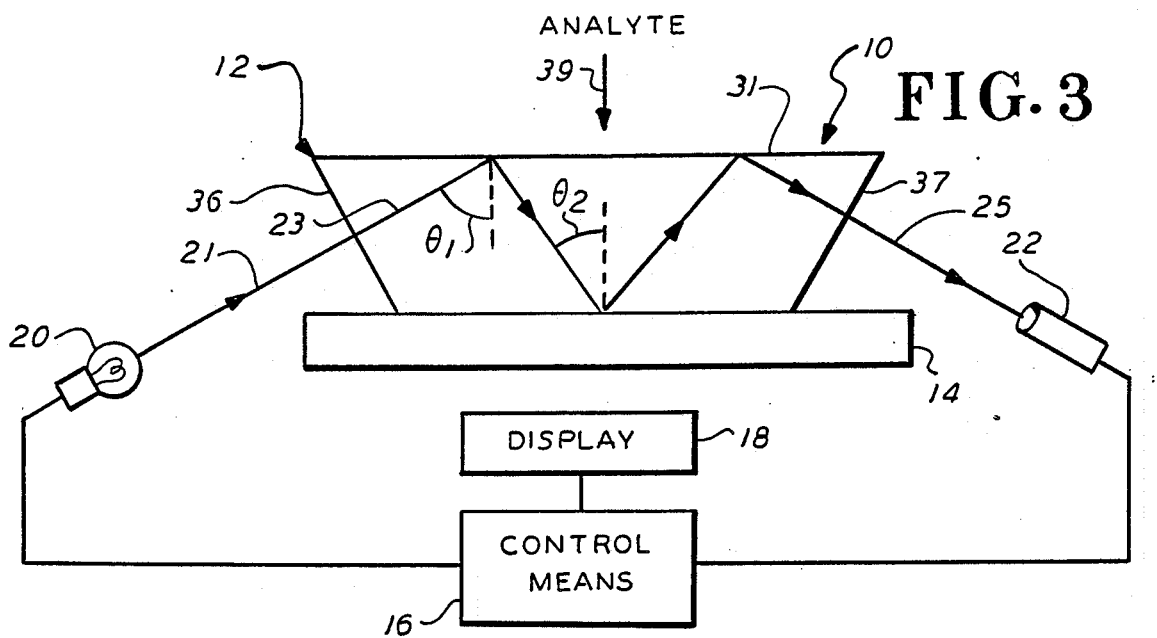
FIG. 3 illustrates a side view of FIG. 2.

In accordance with another aspect of the present invention, and referring now to FIGS. 2 and 3, there is illustrated an apparatus embodiment of the present invention particularly useful for practicing the process of the present invention for detecting or determining analyte; FIG. 2 is a diagrammatical illustration of such apparatus and FIG. 3 is a side view of FIG. 2. The apparatus is indicated by general numerical designation 10 and may include an optically transparent gel body 12, a suitable support 14 for the gel body, control means 16, display or indicating means 18, light beam source 20, and a light beam detector 22; as shown in FIG. 2, the light beam source 20 may be provided, if desired or required, with suitable collimating lenses 24, a filter 26, and the detector 22 may be provided, if desired or required, with suitable collecting lens 28, all as shown. The gel body 12 may be provided with a suitable stand alone prismatic shape, such as by molding, and as is further shown may be provided with a dove prism shape having parallel top and bottom surfaces 31 and 32, parallel side surfaces 33 and 34, and inclined end surfaces 36 and 37; the gel comprising the gel body 12 may be chosen to permit such molding and stand alone characteristic. It will be understood that by knowing the relative index of refraction at the gel body-air interface (interface between the top surface 31 of the gel and the surrounding air and the interface between the gel bottom surface 32 and the air therebetween and the top surface of the support 14) the critical angle $\theta$ for the total internal reflectance of the light beam 21 through the gel body 12 may be determined as taught above, and by transmitting the light beam 21 from the light beam source 20 such that the incident angles $\theta_1$ and $\theta_2$ at which the light beam 21 strikes or contacts the gel body-air interface is above the critical angle $\theta_c$, the light beam 21 will be confined within the gel body and transmitted therethrough by total internal reflectance. To further enhance transmission of the light beam 21 though the gel body 12 by internal reflectance and to eliminate light beam refraction upon entry and exiting the gel body, the gel body is given a prismatic shape (e.g. dove prism shape) and the angle of inclination $\theta_3$ of the entry and exit surfaces is chosen so as to permit the beam of light 21 to enter and exit the gel body perpendicularly with respect to the entry and exit gel surfaces 36 and 37 as well as strike or contact the gel body-air interface above the critical angle $\theta_c$; this may be better seen in FIG. 3 where the leg 23 of the light beam 21 enters the inclined surface 36 of the gel body 12 perpendicularly and contacts the gel body-air interface at an incident angle $\theta_1$ above the critical angle $\theta_c$, and where the leg 25 of the light beam 21 is reflected from the gel body-air interface above the critical angle (angle of incidence equals angle or reflectance) and exits the inclined surface 37 of the gel body 12 perpendicularly. The gel body 12 is provided with a reagent system as taught above and due to the manner of supporting of the gel body by the support 14 a sample portion of an analyte or a portion to be determined or identified, indicated by arrow 39, may be applied to a different surface of the gel body 12 (applied to the top surface 31 of the gel body) than the light beam 21 (applied to the inclined surface 36 of the gel body) thereby overcoming the prior art problem associated with a gel body for determining analyte wherein the analyte and light beam are applied to the same surface which, inter alia, can require the unwanted removal of the analyte prior to application of the light beam for analyte determination and/or the inability to simultaneously apply both analyte and light beam to the gel body thereby restricting efficiency and usability of such prior art.

In practicing the process of the present invention, and referring again to FIGS. 2 and 3, generally, a sample portion or at least a portion of an analyte, as indicated by arrow 39, is applied to the top surface 31 and which diffuses into the gel body changing at least one optical transmissive property of the gel body (changing color, causing or producing a change in turbidity, etc.), the control means 16 operates the light beam source 20 to produce and transmit light beam 21 through the gel body by total internal reflectance as described above whereupon the light beam 21 is modified by the change in transmissive property of the gel body and the light detector 22 receives the modified light beam and transmits a signal to the control means 16 which in turn provides a signal to the display or indicating means 18 to display an indication of the determination of the analyte as determined by the control means 16.

It will be understood by those skilled in the art that the control means 16 may be suitably constructed and operated to provide an end-point determination of the analyte. In this mode, prior to diffusing of the sample portion or at least a portion of the analyte into the gel body, the control means 16 operates the light beam 20 to transmit and pass the light beam 21 into and through the gel body 12 by total internal reflectance for receipt by the light beam detector 22 to provide a first signal to the control means which is suitably stored, and at a later predetermined time subsequent to diffusing of the sample portion or at least a portion of the analyte into the gel body causing a change in optical transmissive property of the gel body, the control means 16 again operates the light beam source 20 to transmit and pass the light beam 21 into and through the gel body by total internal reflectance with the light beam being modified by the change in transmissive property of the gel body, the modified light beam is received by the light beam detector 22 which provides a second signal to the control means 16 which compares the first and second signals to provide a third signal to the display 18 which provides a display indicative of the end-point determination of the analyte. It will be noted from FIGS. 2 and 3 that by passing or transmitting the light beam through a gel body by total internal reflectance the length of the light beam through the body is increased to a length greater than would be provided to a light beam passing through the gel body in a straight line, and hence the accuracy and sensitivity of the analyte determination are enhanced.

Alternatively, it will be understood that the apparatus 10 of FIGS. 2 and 3 may be operated in a mode to provide a kinetic determination of the analyte; it will be understood by those skilled in the art that the term "kinetic" is used in the sense that the analyte determination is made on the basis of a measure of the rate of change of optical transmissive property of the gel body or while such change is "in motion." In this mode, a sample portion, or at least a portion of the analyte, is diffused into the gel body and reacts varyingly with the reagent system therein during a predetermined period of time causing the gel body in turn to undergo a varying change in optical transmissive property during the predetermined period of time. During this predetermined period of time, control means 16 operate the light beam source 20 to cause the light beam 21 to pass into and through the gel by total internal reflectance with the light beam being varyingly modified during such period of time by the varying change in transmissive property of the gel; the varyingly modified light beam is received by the light detector 22 to produce and apply a varying signal to the control means during this predetermined period. The control means in turn computes or measures the rate of change of the varying change in transmissive property of the gel body which rate of change, for example, may be compared with rates of change stored in the control means 16 that different analytes produce upon reaction with the reagent system within the gel body and thereby the analyte may be determined. This determination will cause the control means to provide a signal to the display means indicative, for example, of either the final analyte determination or a varying signal indicative of the rate of change.

It will be further understood by those skilled in the art that the control means 16 may be comprised of suitable control elements known to the art and assembled in the manner known to the art to provide either the above-described end-point mode of analyte determination or measure of rate of change analyte determination. It is believed that patentability resides in the combination of such elements within the control means 16 in further combination with the other structure shown in FIGS. 2 and 3 and combined in accordance with the teachings herein.

Referring again to FIGS. 2 and 3, to assure that the bottom surface 32 of the gel body 12 is not in optical contact with the top surface of the support 14 and that the bottom gel body surface 32 has a gel body-air interface, the top of the support 14 may be provided with suitable upwardly extending, parallel rails (not shown) for supporting the gel body 12 and with the rails extending parallel to the path of the light beam 21 through the gel body and spaced apart so as to reside on either side of the light beam path.

Figure 4:
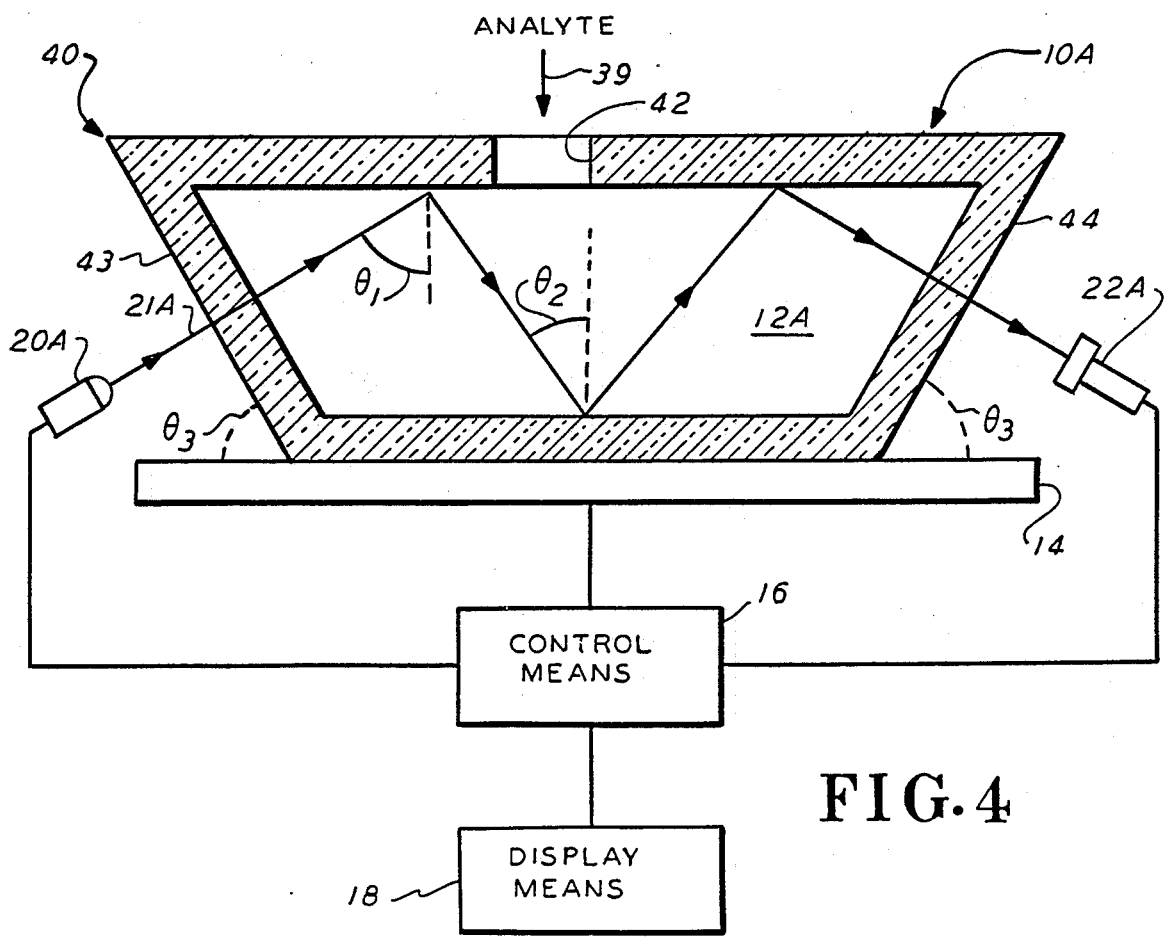
FIG. 4 illustrates another embodiment of the instant invention.

Referring now to FIG. 4, there is illustrated diagrammatically another embodiment, apparatus 10A, embodying the present apparatus invention; structure in this Figure corresponding to structure shown in FIGS. 2 and 3 is numbered correspondingly; the gel body 12A and container 40 are shown in good vertical cross-section, and it will be understood that the container 40 has parallel top and bottom inner and outer surfaces, parallel inner and outer side surfaces, and parallel inclined inner and outer surfaces at either end as shown. In this embodiment, the gel body 12 having a reagent system within is contained within the prismatically shaped cuvette or contained 40 of suitable prismatic shape, such as being provided with a dove prism shape. The container or cuvette 40 of FIG. 4 is made of suitable optically transparent material and includes opposed parallel inner and outer surfaces provided with a prismatic shape, e.g. the shape of a dove prism, as shown. The inner surfaces of the prismatically shaped container or cuvette 40 provide a chamber for receiving the gel body 12A and for providing the gel body with the same prismatic shape; the top of the container 40 may be provided with a suitable opening 42 for permitting entry of a sample portion or at least a portion of the analyte into the cuvette to diffuse with the gel body 12 and react with the reagent system therein causing a change in at least one optical transmissive property of the gel body described above. It will be noted that the respective ends 43 and 44 of the container or cuvette 40 are inclined at an angle $\theta_3$ for the same reasons described above with regard to the inclination of end surfaces 36 and 37 of gel body 12 in FIGS. 2 and 3; also to assure an air-container interface at the bottom surface of the container 40, the container may be supported at its bottom surface as described above with respect to gel body 12 of FIGS. 2 and 3.

In this embodiment, FIG. 4, the light beam 21A, for total internal reflectance through the gel body 12A, is reflected at the interface between the top and bottom surfaces of the gel body and the top and bottom inner surfaces of the container or cuvette 40 as shown, with the light beam 21A striking these interfaces at angles of incidence, $\theta_1$ and $\theta_2$ greater than the critical angle $\theta_c$ taught above; the material (e.g. plastic) of which the container 40 is made is less dense that the gel body 12A and the relative index of refraction at the gel body 12A interface with the top and bottom inner surfaces of the container 40 is less than unity. It will be further understood that, by suitably constructing the control means 16 of FIG. 4, apparatus 10A may be operated in either the end point mode or the kinetic mode for analyte determined as described above with regard to apparatus 10.

Figure 5:
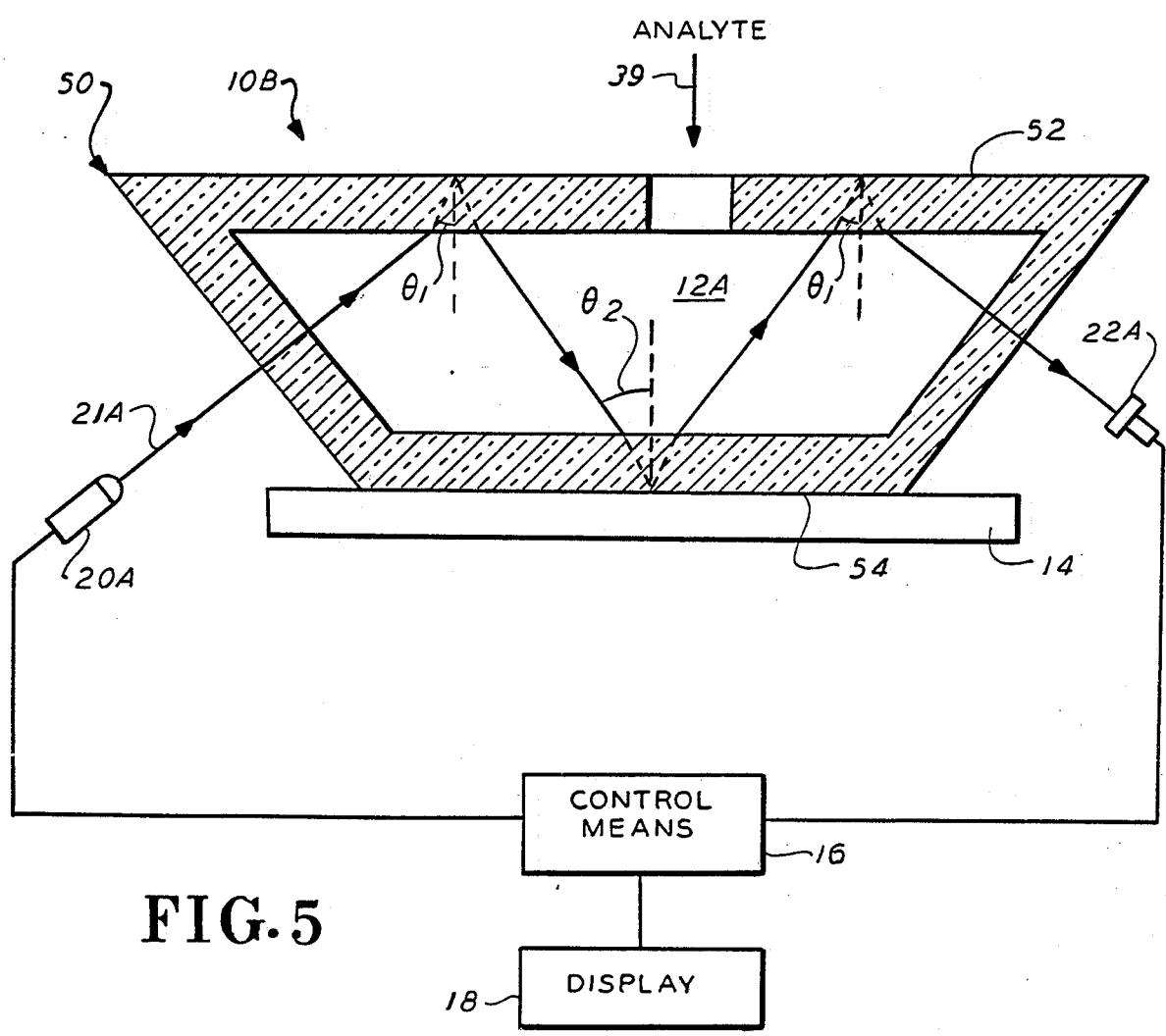
FIG. 5 illustrates yet another embodiment of the instant invention.

A still further alternate embodiment of analyte determiantion apparatus embodying the teachings of the present inventioon is illustrated diagrammatically in FIG. 5; it will be understood that this embodiment is substantially the same as the embodiment 10A illustrated in FIG. 4 except that in this embodiment the total reflectance of the light beam 21A occurs not at the gel body 12A container inner surfaces interface but instead occurs at the interface between the top and bottom outer surfaces of the container 50 with a surrounding medium, such as air. This is because: (i) the gel body 12A is less dense than the material which the container 50 is made and hence the gel body 12A-container 50 interface has a relative index of refraction greater than unity (thus no critical angle for reflectance is possible at this interface), (ii) the container material is more dense that the surrounding air and the relative index of refraction between the top and bottom outer surfaces of the container 50 and the surrounding air is less than unity and hence has a critical angle $\theta_c$ for internal reflectance, and (iii) the angle of incidence $\theta_1$ of the beam of light 21A at the interface between the outer top and bottom surfaces of the container 50 and air is below the critical angle $\theta_c$ for internal reflectance; whereupon, as shown, the light beam 21A is refracted at the interfaces between the gel body 12A and the top and bottom inner surfaces of the container 50 and passes through the container top and bottom walls 52 and 54 and contacts the interfaces between the top and bottom outer surfaces of the container 50 and air at angles of incidence $\theta_1$ and $\theta_2$ above the critical angle $\theta_c$ and is reflected back into the gel body 12A to pass therethrough by total internal reflectance; otherwise, embodiment 10B of FIG. 5 may be operated in the same manner as apparatus 10A of FIG. 4.

Referring again to FIG. 4, an alternative for total internal reflectance of the beam of light 21A through the gel body 12A is to mirror the inner top and bottom surfaces of the container 40 with a suitable mirroring material not reactive with the gel body and reagent system therein; this may be done for example by coating the inner surfaces of the container 40 with a layer of Mylar having one surface aluminized and with the unaluminized Mylar surface being exposed to the gel body.

The term "sample portion" when used in the present application and claims refers to either all or a portion of the sample which contains the analyte. The sample portion which diffuses into the gel may or may not contain the analyte depending on the particular assay. For example, the sample portion which diffuses into the gel may include the analyte and the analyte interacts with the reagent system in the gel to change at least one transmissive property; for example, a glucose assay. As another example, the sample portion which diffuses into the gel may contain a material other than the analyte, which material interacts with the reagent system to change at least one transmissive property which is used to determine analyte; for example, an immunoassay where tracer interacts with the reagent system to determine analyte. Thus, the term "sample portion" as used herein encompasses a sample portion which may or may not include the analyte.

As used herein, the terms "determining analyte" or "determination of analyte" or terms of similar import encompasses both a qualitative determination and/or a quatitative determination.

It will be understood by those skilled in the art that many modifications and variations of the present invention may be made without departing from the sprit and the scope thereof.

What is claimed is:

1. A produce for determining analyte, comprising:
   an optically transparent gel body, said gel body having a first surface portion and a second surface portion; support means for said gel body; and a reagent system within said gel body which in the presence of said analyte which diffuses into the gel body changes a transmissive property of the gel body, said support means supporting said gel body to present said first surface portion for having said sample portion applied thereto and to present said second surface portion for having a beam of light applied thereto for entry into and transmission through the gel, said gel body having the shape of a dove prism to transmit said light beam therethrough by total internal reflectance and said gel body not being an optical fiber.

2. The product of claim 1 wherein the reagent system changes the transmissive properties by changing the light absorption of the gel.

3. The product of claim 2 wherein the reagent system comprises an enzyme and as chromogen.

4. A process for determining analyte in a sample, comprising:
   providing an optically transparent gel body in the shape of a dove prism, said gel body not being an optical fiber and said gel body containing a reagent system which in the presence of analyte changes a transmissive property of the gel body;
   supporting said gel body to present a first surface portion for having said analyte applied thereto and to present a second surface portion for having a beam of light directed thereagainst
   applying a sample containing an analyte to be determined to said first surface portion of said gel body, directing a beam of light against said second surface portion of said gel body to transmit light through said gel body; and detecting light transmitted through the gel body as a determination of analyte.

5. The process of claim 4 wherein the reagent system changes said transmissive property by changing the light absorption of the gel.

6. The process of claim 5 wherein the reagent system comprises an enzyme and a chromogen.

7. The process of claim 4 wherein the gel body is in a container having a surrounding medium, one of the gel body-container interface and container-surrounding medium interface is provided with a relative index of refraction less than unity and wherein said beam of light is directed against said second surface portion for passing through the gel body and contacting one of the interfaces at an angle greater than the critical angle to provide total internal reflectance.

8. The process of claim 7 wherein the reagent system changes the transmissive properties by changing the light absorption of the gel.

9. In an assay for an analyte in a sample employing a tracer and a binder for at least one of the tracer and analyte wherein there is produced in the assay a bound tracer portion and an unbound tracer portion, the improvement comprising:
applying at least the unbound tracer portion to an optically transparent gel body in the form of a dove prism to diffuse the unbound tracer portion into the gel body, said gel body not being an optical fiber and said gel body containing a reagent system which in the presence of tracer changes the transmissive properties of the gel body; and transmitting light through said gel body by total internal reflectance and detecting light transmitted through the gel body as a determination of analyte in the sample.

10. The process of claim 9 wherein the reagent system in the presence of tracer produces a change in color and light transmitted is detected by a change in color.

11. The process of claim 9 wherein the tracer includes an enyzme label and the reagent system interracts with enzyme label to change light absorption of the gel body.

12. The process of claim 11 wherein sample containing bound and unbound tracer is applied to the gel body and unbound tracer diffuses into the gel body.

13. A reagent kit, comprising:
a package, said package containing a tracer; and a gel body in the form of a dove prism, said gel body including a reagent system which in the presence of the tracer changes the transmissive properties of the gel body; and said gel body not being an optical fiber.

14. The kit of claim 13 wherein the tracer includes an enzyme label.

15. The kit of claim 14 wherein the reagent system includes a chromogen.

16. A product for determining analyte, comprising:
an optically transparent container in the shape of a dove prism and having a surrounding medium; an optically transparent gel body within the container and provided with the shape of a dove prism, and a reagent system within said gel body which in the presence of a sample portion containing analyte which diffuses into the gel body changes at least one transmissive property of the gel, at least one of the gel-body container interface or the container-surrounding medium interface having a relative index of refraction greater than unity to reflect back into the gel body a beam of light passing through the gel body and contacting one of the interfaces at an incident angle greater than the critical angle and said gel body not being an optical fiber.

17. The product of claim 16 wherein the reagent system changes the transmissive properties by changing the light absorption of the gel.

18. The product of claim 17 wherein the reagent system comprises an enzyme and a chromogen.

19. The product of claim 17 wherein the reagent system comprises a substrate and a chromogen.

20. The product of claim 17 wherein the reagent system comprises one of an antigen and an antibody.

21. Apparatus for determining analyte, comprising:
an optically transparent gel body in the shape of a dove prism having a first surface portion and a second surface portion and having a reagent system therein which upon at least a portion of said analyte diffusing into said gel body reacts with said analyte portion to change a transmissive property of said gel body, said gel body not being an optical fiber;
light beam source for providing and transmitting a beam of light through said gel body;
light beam detector receiving said light beam after transmission through said gel body and modification of said change in transmissive property and for providing a first output;
control means for operating said light beam source and for receiving said first output to provide a second output indicative of the determination of said analyte;
display means for providing a display of the determination of said analyte upon receipt of said second output; and
support means for supporting the gel body whereby said analyte portion is applied to said first surface and said light beam is applied to said second surface for entry into and transmission through said gel body for receipt by said radiation beam detector.

22. Apparatus according to claim 21 wherein said apparatus is for providing an end-point determination of said analyte, and wherein said control means, prior to diffusing of said analyte portion into said gel body, is for operating said light beam source to pass said light beam into and through said gel and for receipt by said light beam detector to provide a first signal to said control means, and subsequent to the diffusing of said analyte portion into said body and said change in transmissive property of said gel body, said control means for operating said light beam source to pass said light beam into and through said gel body for receipt by said light beam detector to provide a second signal to said control means and said control means for comparing said first and second signals to provide a third signal to said display means to provide a display of said end-point determination of said analyte.

23. Apparatus according to claim 21 wherein said apparatus is for providing a kinetic determination of said analyte, wherein upon at least a portion of said analyte diffusing into said gel body and reacting with said reagent system said gel body undergoing a varying change in a transmissive property during a predetermined period of time, wherein said control means is for operating said light beam source during said predetermined period of time to cause said light beam to pass into and through said gel and be varyingly modified by said varying change in transmissive property and received by said radiation beam to provide a varying signal to said control means to determine the rate of change of said transmissive property during said predetermined period, and said control means for providing said second output to said display means to provide a display of said rate of change.

24. Apparatus according to any one of claims 21, 22 or 23 wherein said support means comprises a prismatically shaped container of optically transparent material provided with a prismatically shaped chamber for receiving said gel body and for providing said gel body with a prismatic shape and to facilitate total reflectance of said light beam through said gel body to enhance the sensitivity and accurancy of said analyte determination and to cause said light beam to enter and exit said container and gel body perpendicularly thereto to eliminate refraction of said light beam upon said entry and exit.

25. Apparatus according to any of claims 21, 22, or 23 wherein said support means comprises a container of optically transparent material including opposed parallel inner and outer surfaces provided with a prismatic shape, said inner surfaces providing a chamber for receiving and providing said gel body with said prismatic shape, wherein said optically transparent container material and said gel body have a predetermined relative index of refraction at the interface therebetween and wherein said light beam source is positioned to transmit said light beam through said container and into said gel body to cause the incident angle of said light beam at said interface to be above the critical angle for total internal reflectance and to cause siad light beam to be transmitted through said gel body by total internal reflectance.

26. Apparatus according to any of claims 21, 22, or 23 wherein said support means comprises a container of optically transparent material including opposed parallel inner and outer surfaces provides with a prismatic shape, wherein said optically transparent container material and a surrounding medium have a predetermined relative index of refraction at the interface therebetween and wherein said light beam source is positioned to transmit said light beam through said container and into said gel body to cause the incident angle of said light beam at said interface to be above the critical angle for total internal reflectance and to cause said light beam to be transmitted through said gel body by total internal reflectance.

27. Apparatus accordiing to claim 25 wherein said container is provided with opposed parallel inner and outer inclined entry and exit surfaces through which said light beam enters and exits said container and wherein said entry and exit surfaces are inclined at a predetermined angle with respect to said interface to cause said light beam to enter and exit said entry and exit surfaces perpendicular thereto to substantially eliminate refraction of said light beam light during entry and exiting of said container.

28. Apparatus according to claim 26 wherein said container is provided with opposed parallel inner and outer inclined entry and exit surfaces through which said light beam enters and exits said container and wherein said entry and exit surfaces are inclined at a predetermined angle with respect to said interface to cause said light beam to enter and exit surfaces perpendicular thereto to substantially eliminate refraction of said light beam during entry and exiting of said container.

29. Product for determining analyte, comrpising:
an optically transparent gel body provided with a dove prismatic shape to cause the transmission of a beam of light therethrough by total internal reflectance, said gel body having first, second and third surface portions and said gel body not being an optical fiber;
a reagent system within said gel body whicch in the presence of a sample portion containing analyte which diffuses into the gel body change a light transmissive property of said gel body;
said first surface portion for having said sample portion applied thereto, said second surface portion for having said beam of light applied thereto, and said third surface portion for having said beam of light exit therethrough after being transmitted through said gel body by total internal reflectance.

* * * * *